United States Patent [19]

Bäther

[11] Patent Number: 4,971,762
[45] Date of Patent: Nov. 20, 1990

[54] DETECTOR DEVICE FOR DETERMINING THE COMPONENTS OF A FLUID SAMPLE AND A METHOD OF PRODUCING THE SAME

[75] Inventor: Wolfgang Bäther, Lübeck, Fed. Rep. of Germany

[73] Assignee: Drägerwerk Aktiengesellschaft, Lübeck, Fed. Rep. of Germany

[21] Appl. No.: 239,347

[22] Filed: Sep. 1, 1988

[30] Foreign Application Priority Data

Sep. 2, 1987 [DE] Fed. Rep. of Germany ....... 3729290

[51] Int. Cl.$^5$ .................... G01N 21/75; G01N 21/78; B05D 1/24
[52] U.S. Cl. ....................................... 422/58; 422/57; 422/86; 422/88; 427/213; 427/215; 427/220
[58] Field of Search ........................... 422/57, 86, 88; 427/213, 215, 220

[56] References Cited

U.S. PATENT DOCUMENTS 4,438,067  3/1984  Siddiqi ................................ 436/66
4,588,612  5/1986  Perkins et al. ..................... 427/220
4,765,962  8/1988  Heim .................................. 422/86

FOREIGN PATENT DOCUMENTS 2155178  8/1987  United Kingdom .

*Primary Examiner*—Robert J. Warden
*Assistant Examiner*—Abanti B. Singla
*Attorney, Agent, or Firm*—Walter Ottesen

[57] ABSTRACT

The invention relates to a detector device for determining components of a sample such as a gaseous sample. The determination is made with reagents which are present in two component quantities separate from each other in the storage condition of the detector device. The component quantities are brought into contact with each other to establish the use condition of the detector device. A simple production and reliable operation of such detector devices is obtained if at least one of the component quantities is contained in a plurality of particles during the storage condition with each particle having a reagent-containing core and an encapsulation surrounding the core. The encapsulation is made of a material which is solid at normal temperature and melts at a higher temperature which is unharmful to the remaining components of the detector device. The detector device is transferred from the storage condition to the use condition by removing the encapsulation by heating. A method for producing the detector device is also disclosed.

11 Claims, 1 Drawing Sheet

DETECTOR DEVICE FOR DETERMINING THE COMPONENTS OF A FLUID SAMPLE AND A METHOD OF PRODUCING THE SAME

FIELD OF THE INVENTION

The invention relates to a detector device for determining the components of a fluid sample and especially of a gaseous sample. The detector device makes this determination with reagents which are present in the form of two component quantities separated from each other when the device is in storage. These component quantities establish the use condition of the detector device when they are brought into contact with each other. The invention also relates to a method for producing such a detector device.

BACKGROUND OF THE INVENTION

Detector devices by means of which gases can be simply, rapidly and inexpensively investigated with respect to the constituents contained therein are known in various forms.

United Kingdom Pat. 2,155,178 discloses a measuring device which operates with an indicator tape containing a reagent. The gas to be tested is drawn through this indicator tape by means of suction. The reagent on the indicator tape react specifically with the constituents of the sample which are to be determined. This leads to a change in coloration which can be photoelectrically detected.

The detector devices are often configured as gas detector tubes. The reagents are arranged in the detector tube so that they have the most intensive contact possible with the gas to be detected when the latter is drawn through the tube by means of suction such as with a special pump.

With the development of detector devices of this kind, the problem is often encountered that several reagents must be utilized which can not be stored together. For this reason, the reagents in the detector devices referred to above are separated into component quantities with each component quantity containing only such reagents which are capable of being stored in contact with each other. This condition of the detector device is characterized as being the storage condition.

Such detector devices are transferred into the use condition only shortly before the use thereof with the previously separated component quantities of the reagents being brought into contact with each other.

In the indicator tape referred to in United Kingdom Pat. No. 2,155,178, three different microcapsules are, for example, provided which contain the component quantities of the reagents and which are destroyed by means of corresponding squeeze rollers of the particular device so that the reagent solutions contained therein flow together and become mixed.

German Pat. No. 713,659 and German Utility Model Registration DE-GM 1,748,816 disclose two different constructions of detector tubes which contain two component chambers separated from each other in the storage condition for two component quantities of reagents which are not capable of common storage. In the detector tube of German Pat. No. 713,659, the connection between the component chambers and therewith the mixing of the reagents contained therein is made possible in that the separation wall contains a plastic plug which is sucked out by the partial vacuum developed when the gas to be tested is drawn in by suction. In DE-GM 1,748,816, the separation is achieved by means of a separation film which is torn by the suction action of the pump. Detector tubes are also known wherein the reagents are contained in separate ampules which must be broken to achieve a transfer into the use condition.

The known detector devices can not be satisfactory in all respects. Especially, they are often complex to produce and/or are not adequately reliable in use.

SUMMARY OF THE INVENTION

In view of the foregoing, it is an object of the invention to provide a detector device wherein the separate storage of mutually incompatible component quantities of the reagents and their transfer into the use condition is made possible by simple means and with good reliability. It is another object of the invention to provide the detector device in the form of a detector tube.

According to a feature of the detector device of the invention, at least one of the component quantities is held in the storage condition in a plurality of particles which each have a reagent-containing core and an encapsulation surrounding the core. The encapsulation is made of a material which is solid at normal temperatures and which melts at a higher temperature which is not harmful for the remaining components of the detector device so that the encapsulation is removable by heating in order to transfer the detector device from the storage condition to the use condition.

The method for producing such a detector device includes as a feature the step of coating the reagent-containing cores with an encapsulation made of a material which has the above-mentioned characteristics and which integrates the particles formed in this manner into the detector device such that the detector device is transferred from the storage condition to the use condition when it is heated to a temperature above the melting point of the encapsulation. When the transfer from the storage condition to the use condition occurs, the reagent components come into contact with each other.

The component quantities of the reagents can contain one or more reagents. The particles contain at least one of the reagent component quantities and are preferably arranged between the remaining reagents in a substantially uniform distribution. When the encapsulation melts, there is then obtained a rapid, homogeneous and thorough mixing of the reagents in contrast to the known detector tubes with several component spaces wherein concentration gradients are unavoidable after opening of the connection between the component spaces.

According to an advantageous feature of the invention, at least two component quantities of the reagents are contained in respective pluralities of particles enclosed with a meltable encapsulation. The particles are arranged so as to be substantially homogeneously mixed with respect to each other.

If the reagent component quantities which are to be incorporated in the particles are solid, the cores can be formed directly from the reagent or from a mixture of the reagent with suitable auxiliary agents and be coated with the encapsulating material.

For reagents which are liquid in their normal state, special measures must be taken to produce cores which are suitable for the encapsulation. Pursuant to a preferred embodiment of the invention, cores of this kind are provided with a porous carrier material. This carrier material is loaded with the reagent (or with the reagent mixture which forms the component quantity), for example, by carrying out the following steps: placing the porous carrier material in a vessel, applying a weak vacuum, and then mixing the same with the reagent and again ventilating. In this way, the reagent is pressed into the pores of the carrier material. The same result can be achieved by heating the carrier material and then subsequently impregnating and allowing the same to cool.

The cores obtained in this manner are coated with the encapsulation in a separate method step with the cores preferably being maintained in movement during the coating process. A fluidized-bed reactor is especially suitable for this purpose.

The encapsulation material is preferably inert with respect to the reactions which occur in the detector device. Paraffin is especially suitable and is chemically very inert and is obtainable in different melting ranges. A very pure paraffin should be utilized. Alternatively, other compounds can, however, also be utilized which are chemically inert with respect to all reagents in the detector device and which have melting temperature ranges corresponding to the particular requirements. For the usual reagents, individual melting temperature ranges between approximately 50° C. and approximately 130° C. are suitable depending upon the particular application of use.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
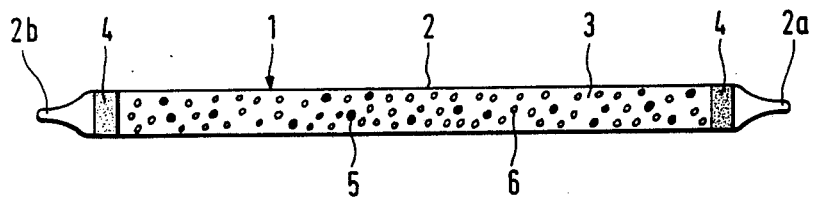
FIG. 1 is a section view taken through a detector device according to the invention in the form of a detector tube; and, FIG. 2 is a section view taken through a particle for the detector device according to the invention.

The detector tube 1 shown in FIG. 1 includes a glass tube 2 having two ends (2a, 2b) which can be snapped off. A charge 3 is arranged in the interior of the tube 2 between gas-permeable holding elements 4 so as to be secure against shaking.

The charge 3 comprises two different types of particles identified by reference numerals 5 and 6. These particles are present in a substantially homogeneous mixture and are so arranged that the gas flow to be tested flows through between the particles when the gas is pumped through the detector tube 1.

Figure 2:
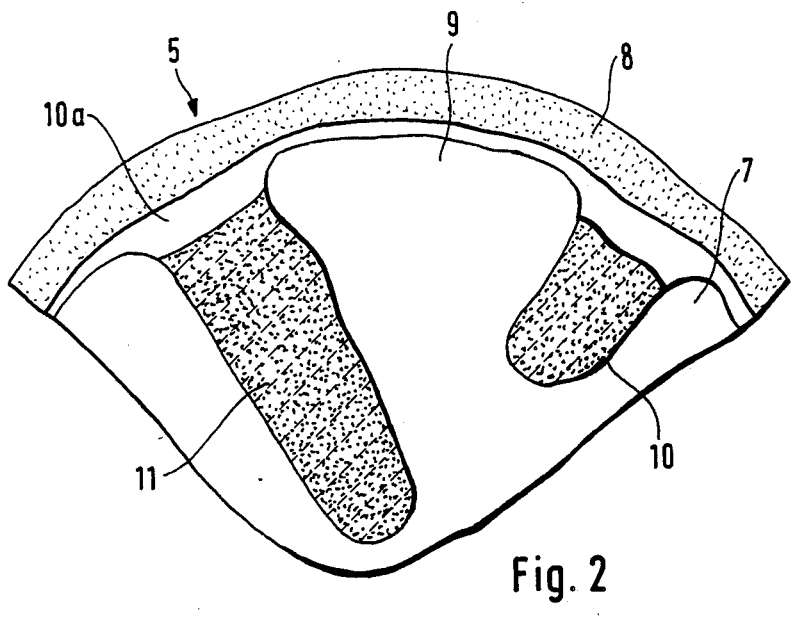

The particle 5 shown in FIG. 2 comprises a core identified in its totality by reference numeral 7 and an encapsulation 8. The core 7 includes a grain 9 of a suitable porous carrier material with the pores being identified by reference numeral 10. The pores 10 are filled with a reagent material 11. The reagent material 11 can be a single reagent or a mixture of various reagents and, if required they can be mixed with auxiliary agents.

The core 7 can also be comprised of several grains connected together and is surrounded by an encapsulation 8 which can be, for example, paraffin. The encapsulation closes the openings 10a of the pores 10 so that the reagent material 11 can not leave the core 7 in the illustrated storage condition of the detector device.

The grain size of the cores 7 lies preferably between 0.2 mm and 3.0 mm and preferably between 0.5 mm and 1.5 mm. The grain size selected in the individual case is dependent especially upon the required resistance of the detector tube. The cores should be as uniform as possible in diameter. In this way, an especially uniform coating is obtained.

Especially those materials which can be utilized as a molecular sieve are suitable as a core material. Furthermore, CPG-glass manufactured by the Schott Company, organized and doing business in the Federal Republic of Germany, has been shown to be suitable.

The size of the pores of the core material should be at least 1 nm.

The detector tube 1 is heated to a temperature above the melting point of the encapsulation 8 in order to transfer the detector tube 1 from the storage condition to the use condition. For this purpose, the detector tube can be placed in a temperature-controlled heating tube. The encapsulation 8 melts and releases the reagent material 11. In this way, the reagent material contained in the respective particles 5 and 6 can come into contact and mix with each other whereby the preparation for the actual detection reaction is made.

The detector tube activated in this manner, usually continues to be used in that the ends (2a, 2b) are snapped off whereafter the detector tube is inserted in a conventional gas detector pump and the gas to be investigated is drawn through the tube by means of suction. A change in color then occurs inside the tube which is dependent upon the composition of the gas and by means of which the determination of the components to be found is made.

In the embodiment shown in FIG. 1, two component quantities of reagents are contained in respective particles 5 and 6. However, in lieu thereof, it is also possible that only one component in the form of encapsulated particles is present which is arranged between the remaining reagents. The remaining reagents can, for example, be present as a powder or as non-encapsulated particles such as lyophilisate.

Although the invention is preferably suited to the application of detector tubes, it can also be utilized together with other kinds of detector devices. Accordingly, the encapsulated particles can, for example, be contained on an indicator tape mixed with the remaining reagents as described in United Kingdom Pat. No. 2,155,178. Here, too, the detector device can be simply activated in that the tape is heated in order to remove the encapsulation of the particles and thereby release the reagents contained in the particles.

The encapsulated particles for the detector device according to the invention can be produced, for example, as described below.

In a first method step, the cores are loaded and for this purpose 100 ml of core material is placed in a 500 ml round-bottom flask. The flask is then evacuated to 300 to 400 mbar. The quantity of reagent component with which the cores are to be charged is added in liquid form via a spray having a valve with the flask being shaken in order to obtain a uniform distribution. The quantity of liquid is dependent upon the liquid absorption capacity of the core material. Depending upon the selected core material, up to 1 ml of reagent liquid can be taken up per 1 ml of core material.

The pressure equalization is carried out, for example, within approximately 10 minutes in the presence of a continued shaking.

In a second and separate method step, the loaded cores are coated with paraffin having a melting range of 65° to 70° C. The paraffin is heated to 100° C. and applied to the reagent-loaded cores located in an Erlenmeyer flask during a very intensive shaking. The intensive shaking should be continued until the paraffin hardens on the core material (approximately 2 minutes). An especially uniform coating is obtained if the core material is somewhat heated (to a maximum of 40° C).

The quantity ratios between core material and paraffin are of special significance. The following quantity ratios have been shown to be especially suitable:

| Core Material Diameter | Paraffin per ml of Core Material |
|---|---|
| 0.5 mm | 0.4 g |
| 1.0 mm | 0.8 g |
| 1.5 mm | 1.2 g |

The loading of the core material described above with the use of a slight vacuum is especially suitable if reagent mixtures with several components are processed. In contrast, if the reagent component quantity to be loaded contains only one constituent, then it can be advantageous to load or charge the carrier material while applying an increased temperature.

For this purpose, for example, 100 ml of core material can be filled into a 500 ml Erlenmeyer flask. Thereafter, the reagent is added in excess (for example, 200 ml) and heated to a boil. After boiling 10 minutes, the batch is allowed to cool and is then filtered away at a reduced pressure.

The detector device of the invention is suitable for detecting any number of constituents in a gaseous sample by selecting the appropriate reagents for encapsulation. For example, to detect the extent of hydrocyanine acid in a gas, three different quantities of particles are provided containing, separate from each other, solutions which only flow together after the detector device is heated to a temperature which melts the paraffin thereby placing the device in the use condition. For the purpose of measuring hydrocyanine acid, the three different quantities are: (1) o-dinitrobenzene in an organic solvent such as CELLOSOLVE; (2) p-nitrobenzaldehyde in an organic solvent such as CELLOSOLVE; and, (3) NaOH solution. The CELLOSOLVE solvents are solvents of the ethylene glycol ether type.

It is understood that the foregoing description is that of the preferred embodiments of the invention and that various changes and modifications may be made thereto without departing from the spirit and scope of the invention as defined in the appended claims.

What is claimed is:

1. A detector device for determining a constituent of a gas sample, the detector device comprising:

a housing holding a first component of a first regent and a second component quantity of a second reagent which is comingled with said first component quantity and yet separated during a storage condition at a first temperature and are brought into contact with each other for preparing said reagents to coact with and detect a constituent of the sample to be investigated;

a plurality of particles holding at least said first reagent during the storage condition;

each of said particles including: a core, and said first reagent contained in said core; and, an impermeable encapsulation surrounding the core holding said first reagent within the particle during the storage condition so as to separate said first reagent from said second reagent; and, said encapsulation being a material solid at said first temperature and melting at a second temperature higher than said first temperature thereby removing the encapsulation and permitting said first and second component quantities to come into contact and coact with each other for detecting said constituent.

2. The detector device of claim 1, said second temperature being selected so as not to alter the chemical properties of said first and second component quantities.

3. The detector device of claim 2, said core being a porous carrier material having a plurality of pores containing said first reagent.

4. The detector device of claim 2, said encapsulation being inert with respect to said reagents.

5. The detector device of claim 2, said encapsulation being paraffin.

6. The detector device of claim 2, said detector device further comprising a housing and said plurality of particles being a first plurality of first particles; and, a second plurality of second particles; and each one of said second particles including: a second core, said second reagent contained in said second core; and an encapsulation made of said solid material and surrounding the second core for holding said second reagent within the second particles during the storage condition; and, said first and second pluralities of particles being mixed together and arranged in said housing so as to cause said first and second reagents to be in mutual contact when said detector device is raised to said second temperature.

7. The detector device of claim 2, said detector device further comprising a tubular housing having respective breakable ends to permit the gaseous sample to flow therethrough; said particles being disposed in said tubular housing so as to cause said particles to conjointly define interspaces therebetween for facilitating the flow of the gaseous sample therethrough.

8. A method of producing a detector device for determining the constituents of a fluid sample such as a gaseous sample, the detector device having a storage condition during which said detector device is stored at a first temperature and a use condition, the detector device including reagents which are present as a first component quality of a first reagent and a second component quantity of a second reagent with said first and second reagents being separated from each other during the storage condition and being brought into mutual contact with each other during the use condition, the method comprising:

forming a plurality of cores containing at least the first reagent;

coating each of the cores with a material for encapsulating the core to prevent the reagent from escaping therefrom during the storage condition, the material being impermeable and solid at said first temperature and melting at a second temperature higher than the first temperature thereby removing the encapsulation and releasing the first reagent; and, arranging the particles with respect to the second reagent in the detector device so as to cause said first reagent and said second reagent to come into contact with each other to transfer the detector device into the use condition when the detector device is raised to said second temperature.

9. The method of claim 8, wherein the cores are formed by charging corresponding cores made of a porous carrier material with the first reagent in liquid form int he presence of a vacuum; and, then coating the cores with said material while imparting continuous motion to said cores.

10. The method of claim 9, wherein the cores are charged at an increased temperature.

11. The method of claim 9, wherein the cores are coated in a fluidized-bed reactor.

* * * * *

UNITED STATES PATENT AND TRADEMARK OFFICE
CERTIFICATE OF CORRECTION

PATENT NO. : 4,971,762

DATED : November 20, 1990

INVENTOR(S) : Wolfgang Bäther

It is certified that error appears in the above-identified patent and that said Letters Patent is hereby corrected as shown below:

In column 1, line 26: delete "reagent" and substitute -- reagents -- therefor.

In column 5, line 49: between "component" and "of" insert -- quantity --.

In column 5, line 49: delete "regent" and substitute -- reagent -- therefor.

In column 6, line 38: delete "quality" and substitute -- quantity -- therefor.

In column 6, line 61: delete "int he" and substitute -- in the -- therefor.

Signed and Sealed this

Twenty-first Day of April, 1992

Attest:

HARRY F. MANBECK, JR.

*Attesting Officer*      *Commissioner of Patents and Trademarks*